US00PP15118P2

(12) United States Plant Patent
Kievit

(10) Patent No.: US PP15,118 P2
(45) Date of Patent: Aug. 31, 2004

(54) CALIBRACHOA PLANT NAMED 'KIECASAL'

(50) Latin Name: *Calibrachoa procumbens*
Varietal Denomination: Kiecasal

(75) Inventor: Christa Kievit, Venhuizen (NL)

(73) Assignee: Kieft Seeds Holland, Venhuizen (NL)

( * ) Notice: Subject to any disclaimer, the term of this patent is extended or adjusted under 35 U.S.C. 154(b) by 0 days.

(21) Appl. No.: 10/666,271

(22) Filed: Sep. 17, 2003

(51) Int. Cl.[7] ..... A01H 5/00
(52) U.S. Cl. ..... Plt./263
(58) Field of Search ..... Plt./263

*Primary Examiner*—Anne Marie Grunberg
*Assistant Examiner*—Annette H Para
(74) *Attorney, Agent, or Firm*—C. A. Whealy

(57) ABSTRACT

A distinct cultivar of Calibrachoa plant named 'Kiecasal', characterized by its uniform, outwardly spreading, mounded and trailing plant habit; freely and continuous branching habit; dense and bushy plant growth habit; freely flowering habit; and numerous pink-colored flowers with darker pink-colored venation.

1 Drawing Sheet

Botanical classification/cultivar designation: *Calibrachoa procumbens* cultivar Kiecasal.

BACKGROUND OF THE INVENTION

The present Invention relates to a new and distinct cultivar of Calibrachoa plant, botanically known as *Calibrachoa procumbens,* and hereinafter referred to by the cultivar name Kiecasal.

The new Calibrachoa is a product of a planned breeding program conducted by the Inventor in Venhuizen, The Netherlands. The objective of the breeding program is to create new trailing Calibrachoas with numerous flowers with attractive flower colors.

The new Calibrachoa originated from a cross-pollination made by the Inventor during the summer of 2000 of a proprietary Calibrachoa selection identified as K138/97, not patented, as the female, or seed parent, with a proprietary Calibrachoa selection identified as K156/97, not patented, as the male, or pollen parent. The new Calibrachoa was selected as a single flowering plant from the resulting progeny by the Inventor in a controlled environment in 2000 in Venhuizen, The Netherlands.

Asexual reproduction of the new cultivar by terminal cuttings in Venhuizen, The Netherlands since 2000 has shown that the unique features of this new Calibrachoa are stable and reproduced true to type in successive generations.

SUMMARY OF THE INVENTION

Plants of the cultivar Kiecasal have not been observed under all possible environmental conditions. The phenotype may vary somewhat with variations in environment such as temperature and light intensity without, however, any variance in genotype.

The following traits have been repeatedly observed and are determined to be the unique characteristics of 'Kiecasal'. These characteristics in combination distinguish 'Kiecasal' as a new and distinct cultivar:

1. Uniform, outwardly spreading, mounded and trailing plant habit.
2. Freely and continuous branching habit; dense and bushy plant growth habit.
3. Freely flowering habit, numerous red-colored flowers.

Plants of the new Calibrachoa differ from the female parent primarily in flower color as plants of the female parent have rose pink-colored flowers. Plants of the new Calibrachoa differ from the male parent in plant habit as plants of the new Calibrachoa are more trailing than plants of the male parent.

Plants of the new Calibrachoa can be compared to plants of the Calibrachoa cultivar Carillon Strawberry Vein, not patented. In side-by-side comparisons conducted in Venhuizen, The Netherlands, plants of the new Calibrachoa differed from plants of the cultivar Carillon Strawberry Vein in the following characteristics:

1. Plants of the new Calibrachoa had a more trailing growth habit than plants of the cultivar Carillon Strawberry Vein.
2. Plants of the new Calibrachoa flowered more continuously than plants of the cultivar Carillon Strawberry Vein.
3. Flowers of plants of the new Calibrachoa resisted fading whereas flowers of plants of the cultivar Carillon Strawberry Vein faded with development.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new Calibrachoa.

The photograph at the top of the sheet comprises a side perspective view of a typical flowering plant of 'Kiecasal' grown in a container.

The photograph at the bottom of the sheet comprises a close-up view of typical flowers and leaves of 'Kiecasal'.

DETAILED BOTANICAL DESCRIPTION

The aforementioned photographs and following observations and measurements describe plants grown in Lompoc, Calif., under commercial practice during the summer and fall in a polycarbonate-covered greenhouse with day temperatures about 21 to 27° C., night temperatures about 16 to 18° C., and light levels about 5,000 to 9,000 foot-candles. Three cuttings were planted per 20-cm container and plants were grown for about 11 weeks. In the following description, color references are made to The Royal Horticultural Society Colour Chart, 1995 Edition, except where general terms of ordinary dictionary significance are used.

Botanical classification: *Calibrachoa procumbens* cultivar Kiecasal.

Parentage:

*Female parent.*—Proprietary *Calibrachoa procumbens* selection identified as K138/97, not patented.

*Male parent.*—Proprietary *Calibrachoa procumbens* selection identified as K156/97, not patented.

Propagation:

*Type cutting.*—Terminal vegetative cuttings.

*Time to initiate roots, summer and winter.*—About 10 days at 20° C.

*Time to develop roots.*—Summer: About 28 days at 20° C. Winter: About 32 days at 20° C.

*Root description.*—Fine, fibrous; white in color.

*Rooting habit.*—Freely branching, moderately dense.

Plant description:

*Form.*—Annual flowering plant; uniform, mounded, outwardly spreading and trailing plant habit; plants eventually becoming hemispherical to spherical in shape. Freely and continuously branching habit with about 12 main lateral branches per plant with lateral branches forming potentially at every node; dense and bushy plant growth habit. Vigorous growth habit.

*Usage.*—Appropriate for hanging baskets, window boxes, patio containers and landscape applications.

*Plant height.*—About 17 cm.

*Plant diameter, single plant.*—About 33 cm.

*Lateral branches.*—Length: About 32 cm. Diameter: About 3.5 mm. Internode length: About 2.5 cm. Texture: Pubescent. Color: 144B.

*Foliage description.*—Arrangement: Before flowering, alternate; after flowering, opposite; simple. Length: About 3 cm. Width: About 9 mm. Shape: Narrowly elliptic. Apex: Broadly acute to rounded. Base: Attenuate. Margin: Entire. Texture, upper and lower surfaces: Mostly glabrous, slightly pubescent along the margins. Venation pattern: Pinnate, arcuate. Color: Developing and mature foliage, upper surface: 146A. Developing and mature foliage, lower surface: 147B. Venation, upper and lower surfaces: 146D. Petiole length: About 8 mm. Petiole diameter: About 1.5 mm. Petiole color: 146C.

Flower description:

*Flower type and habit.*—Salverform flowers; single, axillary. Flowers face mostly upward or outward and are held above the foliage. Flowers persistent.

*Quantity of flowers.*—Very freely flowering, typically about 125 or more open flowers and flower buds per plant.

*Natural flowering season.*—Long day responsive; spring until frost in the autumn; flowering continuous during the flowering period.

*Flower longevity on the plant.*—About 7 to 10 four days.

*Fragrance.*—None detected.

*Flower diameter.*—About 3.5 cm.

*Flower depth (height).*—About 3 cm.

*Flower buds (showing color).*—Length: About 2.4 cm. Diameter: About 6 mm. Shape: Elongated oblong. Color: More gray than 84B.

*Corolla.*—Arrangement/appearance: Single whorl of five petals, fused into flared trumpet with distinct clefts between petal lobes. Petal length from throat: About 1.5 cm. Petal width: About 1.7 cm. Petal shape: Roughly spatulate or fan-shaped. Petal apex: Obtuse. Petal margin: Entire. Petal texture: Smooth, satiny. Color: Petal, upper surface, when opening: 70B. Petal, lower surface, when opening: 186D. Petal, upper surface, fully opened: 70C; towards throat, 74A to 74B; color becoming closer to 70D with subsequent development. Petal, lower surface, fully opened: 186D. Flower throat (inside): 12A. Flower tube (outside): 186D. Venation, upper petal surface: Close to 74A to 74B. Venation, lower petal surface: Close to 186D. Venation, throat and tube: Same as throat and tube colors.

*Sepals.*—Arrangement/appearance: Single whorl of five sepals fused at base, star-shaped. Length: About 1 cm. Width: About 3 mm. Shape: Elliptic to lanceolate. Apex: Acute. Margin: Entire. Texture, upper and lower surfaces: Pubescent. Color, immature, upper and lower surfaces: 146A. Color, mature, upper and lower surfaces: 146A.

*Peduncles.*—Length: About 3.2 cm. Width: About 1 mm. Angle: About 30 to 45° to the stem. Strength: Strong. Texture: Pubescent. Color: 144B.

*Reproductive organs.*—Stamens: Quantity/arrangement: Five. Anther shape: Ovoid. Anther length: Less than 1 mm. Anther color: 12A. Pollen amount: Scarce. Pollen color: 12A. Pistils: Quantity: One. Pistil length: About 1.1 cm. Stigma shape: Anvil-shaped. Stigma color: 144B. Style length: About 8 mm. Style color: 144C. Ovary color: 145A.

*Seed/fruit.*—Seed and fruit production has not been observed.

Disease/pest resistance: Plants of the new Calibrachoa have not been noted to be resistant to pathogens or pests common to Calibrachoa.

It is claimed:

1. A new and distinct cultivar of Calibrachoa plant named 'Kiecasal', as illustrated and described.

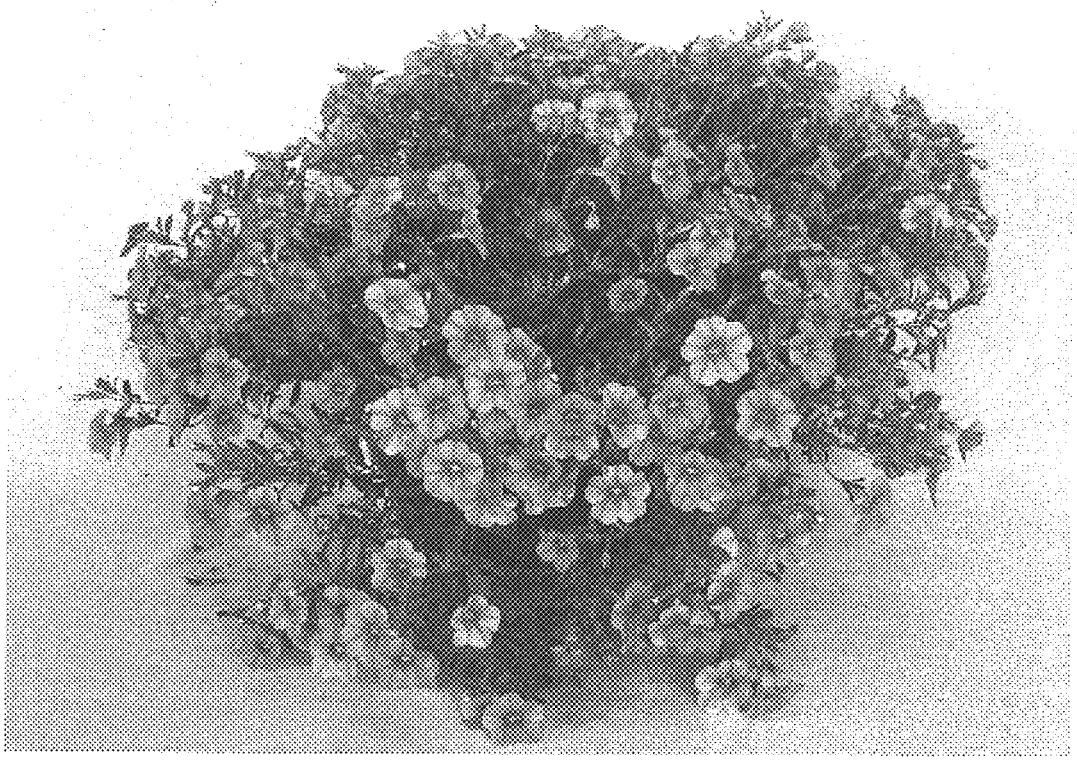
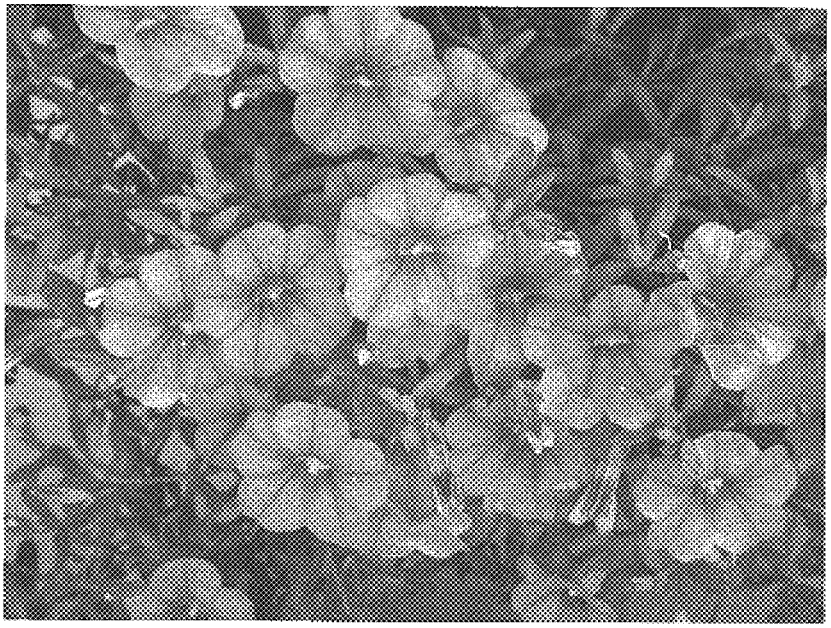

* * * * *